US006123956A

United States Patent [19]

Baker et al.

[11] Patent Number: 6,123,956

[45] Date of Patent: Sep. 26, 2000

[54] METHODS FOR UNIVERSALLY DISTRIBUTING THERAPEUTIC AGENTS TO THE BRAIN

[75] Inventors: Keith Baker, 180 Summer St., Danvers, Mass. 01923; Mark Kieras, Newburyport, Mass.; Martin Redmon, Marlborough, Mass.; Daniel Pratt, Amesbury, Mass.

[73] Assignee: Keith Baker, Danvers, Mass.

[21] Appl. No.: 09/112,708

[22] Filed: Jul. 9, 1998

Related U.S. Application Data

[60] Provisional application No. 60/052,103, Jul. 10, 1997.

[51] Int. Cl.[7] .................... A61F 2/02; A61F 9/50

[52] U.S. Cl. .................... 424/426; 424/499; 424/501; 424/502

[58] Field of Search .................... 424/426, 499, 424/501, 502

[56] References Cited

U.S. PATENT DOCUMENTS

| | | | |
|---|---|---|---|
| 4,078,052 | 3/1978 | Papahadjopoulos | 424/36 |
| 4,089,801 | 5/1978 | Schneider | 252/316 |
| 4,145,410 | 3/1979 | Sears | 424/19 |

(List continued on next page.)

| | | | |
|---|---|---|---|
| 5,601,835 | 2/1997 | Sabel et al. | 424/424 |

FOREIGN PATENT DOCUMENTS

| | | |
|---|---|---|
| 0 731 108 A1 | 11/1996 | European Pat. Off. . |
| 0 260 415 B1 | 3/1998 | European Pat. Off. . |
| 2 050 287 | 1/1981 | United Kingdom . |
| WO 9426250 | 11/1984 | WIPO . |
| WO 9309802 | 5/1993 | WIPO . |
| WO 9600537 | 1/1996 | WIPO . |
| WO 9703652 | 2/1997 | WIPO . |

OTHER PUBLICATIONS

Boer, G.J., et al., (1984) "Successful ventricular application of the miniaturized controlled–delivery Accurel technique for sustained enhancement of cerebrospinal fluid peptide leves in the rat", *Journal of Neuoscience Methods,* vol. 11, pp. 281–289;.

Chan, P.H., et al., (1987) "Protective Effects of Liposome–Entrapped Superoxide Dismutase on Posttraumatic Brain Edema", *Annals of Neurology,* vol. 21(6), pp. 540–547;.

Freeman, A.I. et al., (1986) "Targeted Drug Delivery", *Cancer,* vol. 58, pp. 573–583;.

Fresta, M et al., (1994) "Liposomes as In–vivo Carriers for Citicoline: Effects on Rat Cerebral Post–ischaemic Reperfusion", *J. Pharm. Pharmacol.,* vol. 46, pp. 974–981;.

Gombotz, W.R., et al., (1995) "Bioderadable Polymers for Protein and Peptide Drug Delivery", *Bioconjugate Chem,* vol. 6, pp. 332–351;.

Jalsenjak, et al., (1988) "Development of biodegradable microcapsules for controlled drug release release into the brain", *Acta. Pharm. Jugosl.,* vol. 38(4), pp. 297–305;.

Lazorthes, Y. et al., (1991) "Advances in Drug Delivery Systems and Applications in Neurosurgery", *Adv Tech Stand Neurosung,* vol. 18, pp. 143–192;.

(List continued on next page.)

*Primary Examiner*—Carlos A. Azpuru

*Attorney, Agent, or Firm*—Elizabeth A. Hanley; Lahive & Cockfield, LLP

[57] ABSTRACT

A method for universally distributing a therapeutic agent, in an encapsulated form, to the brain of a subject using intrathecal administration, excluding the lumbar region, is described. Methods for treating stroke and/or Traumatic Brain Injury (TBI) are also described. The methods involve intrathecal administration into the cerebrospinal fluid of a subject, of a therapeutic agent in an encapsulated form. Pharmaceutical compositions intended for the amelioration of stroke and/or Traumatic Brain Injury (TBI) are also described. The pharmaceutical compositions comprise a therapeutic agent encapsulated in a pharmaceutically acceptable polymer, suitable for injection into the cerebrospinal fluid of a subject suffering from stroke and/or Traumatic Brain Injury (TBI).

22 Claims, 2 Drawing Sheets

Pump Delivery of Superoxide Dismutase

% Infarction 0 1 2 3 4 5 6 7 8 9 10 11 12

Control n=11 Lo n=9 Hi n=10

Gel Foam Delivery of SOD

% Infarction 0 2 4 6 8 10 12

Control n=4 Lo n=5 Hi n=5

Experimental Groups

Control = Saline

Lo Dose = 6,800 units /ml

Hi Dose = 13,600 units /ml

U.S. PATENT DOCUMENTS

| | | | |
|---|---|---|---|
| 4,224,179 | 9/1980 | Schneider | 252/316 |
| 4,235,871 | 11/1980 | Papahadjopoulos et al. | 424/19 |
| 4,310,506 | 1/1982 | Baldeschwieler et al. | 424/1 |
| 4,394,372 | 7/1983 | Taylor | 424/85 |
| 4,522,803 | 6/1985 | Lenk et al. | 424/1.1 |
| 4,588,578 | 5/1986 | Fountain et al. | 424/1.1 |
| 4,599,227 | 7/1986 | Dees et al. | 424/38 |
| 4,610,868 | 9/1986 | Fountain et al. | 424/1.1 |
| 4,619,913 | 10/1986 | Luck et al. | 514/2 |
| 4,752,425 | 6/1988 | Martin et al. | 264/4.6 |
| 4,769,250 | 9/1988 | Forssen | 424/450 |
| 4,781,871 | 11/1988 | West, III et al. | 264/4.3 |
| 4,813,399 | 3/1989 | Gordon | 600/12 |
| 4,833,148 | 5/1989 | Olney | 514/270 |
| 4,837,218 | 6/1989 | Olney | 514/646 |
| 4,861,627 | 8/1989 | Mathiowitz et al. | 427/213 |
| 4,883,666 | 11/1989 | Sabel et al. | 424/422 |
| 4,898,734 | 2/1990 | Mathiowitz et al. | 424/426 |
| 4,906,637 | 3/1990 | Faden | 514/282 |
| 4,920,016 | 4/1990 | Allen et al. | 424/450 |
| 4,945,097 | 7/1990 | Olney | 514/318 |
| 4,978,668 | 12/1990 | Babbs et al. | 514/258 |
| 5,000,959 | 3/1991 | Iga et al. | 424/450 |
| 5,010,197 | 4/1991 | Ron et al. | 528/328 |
| 5,021,200 | 6/1991 | Vanlerberghe et al. | 264/4.3 |
| 5,025,032 | 6/1991 | Carney et al. | 514/400 |
| 5,055,470 | 10/1991 | Boissard et al. | 514/252 |
| 5,057,494 | 10/1991 | Sheffield | 514/12 |
| 5,077,056 | 12/1991 | Bally et al. | 424/450 |
| 5,204,112 | 4/1993 | Hope et al. | 124/450 |
| 5,208,021 | 5/1993 | Johnson et al. | 424/85.91 |
| 5,211,955 | 5/1993 | Legros et al. | 424/450 |
| 5,225,212 | 7/1993 | Martin et al. | 424/450 |
| 5,258,453 | 11/1993 | Kopecek et al. | 525/54.1 |
| 5,330,768 | 7/1994 | Park et al. | 424/501 |
| 5,336,493 | 8/1994 | Poznansky et al. | 424/94.2 |
| 5,342,940 | 8/1994 | Ono et al. | 544/218 |
| 5,360,610 | 11/1994 | Tice et al. | 424/426 |
| 5,395,822 | 3/1995 | Izumi et al. | 514/3 |
| 5,401,755 | 3/1995 | Rice et al. | 514/336 |
| 5,455,044 | 10/1995 | Kim et al. | 424/450 |
| 5,487,897 | 1/1996 | Polson et al. | 424/426 |
| 5,527,822 | 6/1996 | Scheiner | 514/465 |
| 5,554,767 | 9/1996 | Wang et al. | 548/496 |
| 5,576,018 | 11/1996 | Kim et al. | 424/450 |

OTHER PUBLICATIONS

Muizelaar, P.J., et al., (1993) "Cerebral Ischemia–Reperfusijn Injury After Severe Head Injury and Its Possible treatment With Polyethyleneglycol–Superoxide Dismutase", *Annals of Emergency Medicine,* vol. 22(6), pp. 1014–1021;.

Myseros J.S., et al., (1995) "The Rationale for Glutamate Antagonists in the Treatment of Traumatic Brain Injury", *Annals New York Academy of Sciences,* vol. 765, pp. 262–271;.

Streit, W.J., et al., (1995) "The Brain's Immune System", *Scientific American,* vol. 273, pp. 54–61;.

Ommaya, A.L., (1984) "Implantable Devices for Chronic Access and Drug Delivery to the Central Nervous System", *Cancer Durg Delivery,* vol. 1(2), pp. 169–179;.

Control = Saline
Lo Dose = 6,800 units /ml
Hi Dose = 13,600 units /ml

METHODS FOR UNIVERSALLY DISTRIBUTING THERAPEUTIC AGENTS TO THE BRAIN

RELATED APPLICATIONS

This application claims priority under 35 U.S.C. 119(c) of U.S. provisional application No. 60/052,103, filed Jul. 10, 1997, incorporated herein by reference in its entirety.

FIELD OF THE INVENTION

This invention relates to methods for universally distributing therapeutic agents to the brain.

BACKGROUND OF THE INVENTION

Diseases of the central nervous system (CNS) are widespread. The National Institute of Mental Health recently estimated that neurological disorders affect 22% of the adult population in the United States and account for 30% of the total health care budget each year.

Traumatic Brain Injury (TBI), and Stroke are such CNS diseases and are characterized by the need for immediate short term drug therapy. Traumatic Brain Injury (TBI) is caused primarily by a traumatic blow to the head causing damage to the brain, often without penetrating the skull. The initial trauma can result in expanding hematoma, subarachnoid hemorrhage, cerebral edema, raised intracranial pressure (ICP), and cerebral hypoxia, which can, in turn, lead to severe secondary events due to low cerebral blood flow (CBF). Half of the people with TBI die before reaching the hospital and from those that survive, a large percentage suffer serious neurologic disorders.

Stroke is the destruction of brain tissue due to impaired blood supply caused by intracerebral hemorrhage, thrombosis (clotting), or embolism (obstruction caused by clotted blood or other foreign matter circulating in the bloodstream). Stroke is a common cause of death in the United States. The deleterious effects of a stroke are comparable to those caused by TBI.

The use of drugs in neurological illness has been studied extensively over the last century. As a result, many therapeutic agents exist today for the treatment of central nervous system (CNS) diseases including Traumatic Brain Injury (TBI), and Stroke. These include: (a) nonsteroidal anti-inflammatory agents (aspirin, acetaminophen, indomethacin, ibuprofen), (b) steroid anti-inflammatory agents (cortisone, prednisone, prednisolone, dexamethasone), (c) antioxidants (superoxide dismutase, catalase, nitric oxide, mannitol), (d) calcium channel blockers (nimodipine, nifedipine, verapamil, nicardipine, isradipine), and (e) neurotrophic factors (endorphins, citicholine).

However, delivering a drug to a therapeutic site of action within the central nervous system (CNS) can be very difficult because of the numerous chemical and physical barriers which must be overcome in order for such a delivery to be successful. The blood brain barrier (BBB) presents the primary obstacle in delivering drugs to the brain. Other limiting parameters involve the short half-life of drugs and the lack of appropriate drug concentrations reaching a localized area in the brain. Currently, attempts are being made to deliver drugs to the brain via either disruption of the BBB through chemical means, intracerebral delivery using infusion pumps, or direct delivery to the CNS through implantation of fetal neural tissue. Each of these methods have possible deficiencies as evidenced by toxic side-effects, dimensional complications, lack of reliability and high cost.

To date, methods for delivering drugs to the brain have not been completely effective.

SUMMARY OF THE INVENTION

The present invention pertains to a method for universally distributing a therapeutic agent to the brain. The method involves administering to a subject a therapeutic agent such that universal distribution of the agent to the brain occurs. The therapeutic agent is administered by introduction into the cerebrospinal fluid of the subject, in an encapsulated form.

In a preferred embodiment, the method of the invention is used to treat a subject suffering from stroke. In another preferred embodiment, the method of the invention is used to treat a subject suffering from Traumatic Brain Injury (TBI).

Another aspect of the invention pertains to a pharmaceutical composition intended for administration into the cerebrospinal fluid of a subject. The pharmaceutical composition consists of a therapeutic agent encapsulated in a pharmaceutically acceptable polymer. The therapeutic agent is present at therapeutically effective concentrations which, if introduced into the cerebrospinal fluid of a subject suffering from stroke or TBI will ameliorate the disorder.

The method of the invention is a highly efficient, safe and cost effective method of universally distributing sufficient concentrations of a therapeutic agent to the brain. The present invention overcomes limitations of existing methods for delivering drugs to the brain, such as toxic side effects, dimensional complications, lack of reliability, and high cost.

Other features and advantages of the invention will be apparent from the following detailed description, and from the claims.

DETAILED DESCRIPTION

Figure 1:
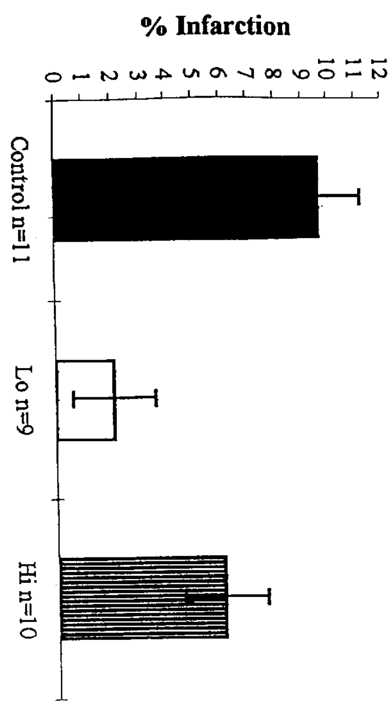
FIG. 1 is a graph depicting local delivery of superoxide dismutase in the cerebrospinal fluid (CSF) of the MCA-O rat either via a pump (left graph) or by injection after encapsulation in a polymeric delivery vehicle (gel foam) (right graph). Three groups of animals were used: A saline control (black bar),a low SOD delivery dose (6,800 units/ml) (white bar) and a high SOD delivery dose (13,600 units/ml) (striped bar).
Figure 1:
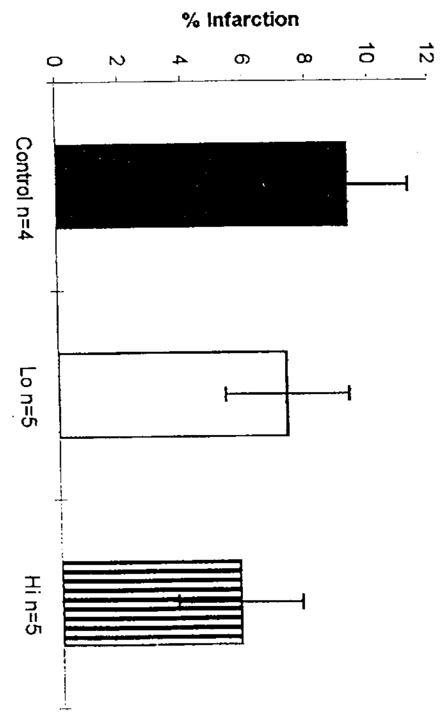

This invention pertains to a method for universally distributing a therapeutic agent to the brain. The method involves administering to a subject a therapeutic agent such that universal distribution of the agent to the brain occurs. The therapeutic agent is administered by introduction into the cerebrospinal fluid of the subject, in an encapsulated form. In a preferred embodiment, the method of the invention is used to treat a subject suffering from stroke. In another preferred embodiment, the method of the invention is used to treat a subject suffering from Traumatic Brain Injury (TBI).

As used herein the language "universally distributing a therapeutic agent to the brain" is intended to include distribution such that the therapeutic agent is distributed to many areas of the brain, for example, resulting in the treatment of a targeted condition. This distribution can be such that the therapeutic agent is distributed to the major parts of the brain, including the two cerebral hemispheres, the cerebellum and the mid-brain. The distribution of the therapeutic agent can be substantially uniform or can be completely uniform.

As used herein, the term "therapeutic agent" is intended to include agents suitable for treating a targeted condition of the brain and capable of being delivered in active form, in vivo using the methods of the invention. The ordinarily skilled artisan would be able to select appropriate art-recognized therapeutic agents for a particular disease or condition targeted for treatment. Examples of such agents include drugs, antibiotics, enzymes, chemical compounds, mixtures of chemical compounds, biological macromolecules and analogs thereof. Similar substances are known or can be readily ascertained by one of skill in the art. One skilled in the art can look to Harrison's Principles of Internal Medicine, Thirteenth Edition, Eds. T. R. Harrison et al. McGraw-Hill New York, N.Y.; and the Physicians Desk Reference 50th Edition 1997, Oradell New Jersey, Medical Economics Co., the complete contents of which are expressly incorporated herein by reference, to determine appropriate therapeutic agents for delivery to the brain for treatment of a targeted condition or disease, for example, for the treatment of stroke or TBI. Examples of therapeutic agents for the treatment of stroke and/or TBI are described in detail below.

As used herein, the term "subject" is intended to include mammals susceptible to or having the disease or condition being treated or targeted for treatment using the methods of the invention. As such the invention is useful for the treatment of humans, domesticated animals, livestock, zoo animals, and the like. Examples of subjects include humans, cows, cats, dogs, goats, and mice. In preferred embodiments the present invention is used for treating human subjects.

As used herein the language "to the brain for treatment" is intended to include treatment of any disorder or condition in need of treatment characterized by universal distribution of a therapeutic agent to the brain. In a preferred embodiment, the method of the invention is used to treat a subject suffering from a disorder, disease or condition of the brain which is characterized by the need for immediate short term drug therapy. "Immediate short term drug therapy" is intended to include therapy within 24 hours, preferably within 16 hours, more preferably within 8 hours, even more preferably within 2 hours.

As used herein, the term "stroke" is art recognized and is intended to include sudden diminution or loss of consciousness, sensation, and voluntary motion caused by rapture or obstraction (e.g. by a blood clot) of an artery of the brain. The method involves administering to a subject a therapeutic agent such that universal distribution of the agent to the brain occurs, wherein the therapeutic agent is administered by introduction into the cerebrospinal fluid of the subject, in an encapsulated form.

In another preferred embodiment, the method of the invention is used to treat a subject suffering from Traumatic Brain Injury (TBI). As used herein, the term "Traumatic Brain Injury" is art recognized and is intended to include the condition in which, a traumatic blow to the head causes damage to the brain, often without penetrating the skull. Usually, the initial trauma can result in expanding hematoma, subarachnoid hemorrhage, cerebral edema, raised intracranial pressure (ICP), and cerebral hypoxia, which can, in turn, lead to severe secondary events due to low cerebral blood flow (CBF). The method involves administering to a subject a therapeutic agent such that universal distribution of the agent to the brain occurs, wherein the therapeutic agent is administered by introduction into the cerebrospinal fluid of the subject, in an encapsulated form.

Therapeutic Agents

Among the therapeutic agents which may be micro encapsulated and administered into the cerebrospinal fluid according to the present invention can be, preferably, anti-inflammatory agents. As used herein the term "anti-inflammatory agents" refers to any agent which possesses the ability to reduce or eliminate cerebral edema (fluid accumulation), cerebral ischemia, or cell death caused by traumatic brain injury (TBI) or stroke. Categories of anti-inflammatory agents include:

a) Free radical scavengers and antioxidants, which act to chemically alter (dismutate) or scavenge the different species of oxygen radicals produced due to ischemic and trauma associated events. Unless dismutated or scavenged, these highly reactive free radicals cause the peroxidation (breakdown) of cell membrane phospholipids (lipid peroxidation) and the oxidation of cellular proteins and nucleic acids leading to severe tissue damage and death of neurons. Examples of such drugs are superoxide dismutase, catalase, nitric oxide, mannitol, allopurinol, dimethyl sulfoxide.

b) Nonsteroidal anti-inflammatory drugs (NSAIDS), which act to reduce cell migration, caused by ischemic and trauma associated events, and therefore slow down edema formation, as well as provide pain relief. Examples of such drugs are aspirin, acetaminophen, indomethacin, ibuprofen.

c) Steroidal anti-inflammatory agents (Glucocorticoids, Hormones), which can enhance or prevent the immune and inflammatory process and inhibit lipid peroxidation as seen in the events that occur during oxygen radical formation.

Examples of such drugs are cortisone, prednisone, prednisolone, dexamethasone. The most well known of these is dextramethasone which has been used for reduction of cerebral edema after TBI.

d) Calcium channel blockers, which act to prevent excess calcium from entering the cell during cerebral ischemia. Some of these drugs also have other beneficial effects on increasing cerebral blood flow to the brain. Examples of such drugs are nimodipine, nifedipine, verapamil, nicardipine.

e) NMDA antagonists, which block the NMDA receptor site for glutamate, a neurotransmitter released excessively during ischemia. Excess glutamate can activate the NMDA receptors leading to increase firing which will in turn cause cell swelling and an influx of calcium leading to cell death. Examples of such drugs are magnesium sulfate and dextromethorphan, actually an opioid analogue.

Finally, citicholine can be used. Citicholine prevents toxic free fatty acid accumulation, promotes recovery of brain function by providing two components, cytidine and choline, required in the formation of nerve cell membrane, promoting the synthesis of acetylcholine, a neurotransmitter associated with cognitive function.

The therapeutic agents can be used alone or in combination with one or more other therapeutic agents to achieve a desired effect.

Pharmaceutically Acceptable Polymers

In the method of the invention, the therapeutic agent or combinations thereof can be encapsulated in one or more pharmaceutically acceptable polymers, to form a microcapsule, microsphere, or microparticle, terms used herein interchangeably. As used herein the term "encapsulated" refers to a process of physically entrapping a therapeutic agent into a polymeric matrix, without changing its chemical characteristics. This definition is provided in order to differentiate the process of preparing the therapeutic agent-polymer complex, from chemical conjugation or cross-linking which, in many cases, can alter the nature of the therapeutic agent. The term "encapsulated" is also intended to include situations in which the therapeutic agent is not completely encapsulated in the polymeric matrix, that is, situations in which part of the therapeutic agent is present on the surface of the polymeric matrix.

Microcapsules, microspheres, and microparticles are conventionally free-flowing powders consisting of spherical particles of 2 millimeters or less in diameter, usually 500 microns or less in diameter. Particles less than 1 micron are conventionally referred to as nanocapsules, nanoparticles or nanospheres. For the most part, the difference between a microcapsule and a nanocapsule, a microsphere and a nanosphere, or microparticle and nanoparticle is size; generally there is little, if any, difference between the internal structure of the two. In one aspect of the present invention, the mean average diameter is less than about 45 $\mu$m, preferably less than 20 $\mu$m, and more preferably between about 0.1 $\mu$m and about 10 $\mu$m. As used in the present invention, the microcapsule, or nanocapsule, has its encapsulated therapeutic agent material centrally located within a wall-forming polymeric material.

In addition, microspheres encompass "monolithic" and similar particles in which the therapeutic agent is dispersed throughout the particle; that is, the internal structure is a matrix of the therapeutic agent and a pharmaceutically acceptable polymer.

The terms "polymer" or "polymeric" are art-recognized and include a structural framework comprised of repeating monomer units which is capable of delivering a therapeutic agent such that treatment of a targeted condition occurs. The terms also include copolymers and homopolymers e.g., synthetic or naturally occurring. Linear polymers, branched polymers, and cross-linked polymers are also meant to be included.

Preferred polymeric materials suitable for forming the microparticles employed in the present invention, include naturally derived polymers such as albumin, alginate, cellulose derivatives, collagen, fibrin, gelatin, and polysacaccharides, as well as synthetic polymers such as polyesters (PLA, PLGA), polyethylene glycol, poloxomers, polyanhydrides, and pluronics. These polymers are biocompatible with the nervous system, including the central nervous system, they are biodegradable within the central nervous system without producing any toxic byproducts of degradation, and they possess the ability to modify the manner and duration of drug release by manipulating the polymer's kinetic characteristics. As used herein, the term "biodegradable" means that the polymer will degrade over time by the action of enzymes, by hydrolytic action and/or by other similar mechanisms in the body of the subject. As used herein, the term "biocompatible" means that the polymer is compatible with a living tissue or a living organism by not being toxic or injurious and by not causing immunological rejection.

Microspheres made with these and similar acceptable polymers are sufficiently resistant to chemical and/or physical destruction by the environment of use, so that they can protect the therapeutic agents from degradation and they can release drugs at a controlled rate over a predesired time. Polymers can be prepared using methods known in the art (Sandler, S. R.; Karo, W. *Polymer Syntheses*; Harcourt Brace: Boston, 1994; Shalaby, W.; Ikada, Y.; Langer, R.; Williams, J. *Polymers of Biological and Biomedical Significance* (ACS *Symposium Series* 540; American Chemical Society: Washington, D.C., 1994). Polymers can be designed to be flexible; the distance between the bioactive sidechains and the length of a linker between the polymer backbone and the group can be controlled. Other suitable polymers and methods for their preparation are described in U.S. Pat. Nos. 5,455,044 and 5,576,018, the contents of which are incorporated herein by reference.

The polymeric microcapsules are preferably formed by dispersion of the therapeutic agent within liquified polymer, as described in U.S. Ser. No. 07/043,695, filed Apr. 29, 1987, U.S. Pat. No. 4,883,666, the teachings of which are incorporated herein by reference. The properties and characteristics of the microcapsules are controlled by varying such parameters as the reaction temperature, concentrations of polymer and therapeutic agent, types of solvent used, and reaction times.

In addition to the therapeutic agent and the pharmaceutically acceptable polymer, the encapsulated therapeutic agent used in the method of the invention can comprise additional pharmaceutically acceptable carriers and/or excipients. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for injection into the cerebrospinal fluid. Excipients include pharmaceutically acceptable stabilizers and disintegrants.

Administration of the Encapsulated Therapeutic Agent

The microspheres can easily be suspended in aqueous vehicles and injected through conventional hypodermic needles. Prior to injection, the microspheres can be sterilized with, preferably, gamma radiation or electron beam sterilization.

Preferably, the encapsulated therapeutic agent described herein is administered to the subject in the period from the time of injury to 100 hours, preferably within 24 hours, and more preferably within 6 to 12 hours after the traumatic brain injury (TBI) or stroke has occurred.

In a preferred embodiment of the invention, the therapeutic agent, in an encapsulated form, is administered into a subject intrathecally. As used herein, the term "intrathecal administration" is intended to include delivering a therapeutic agent encapsulated in a pharmaceutically acceptable polymer directly into the cerebrospinal fluid of a subject, by techniques including lateral cerebroventricular injection through a burrhole or cisternal or lumbar puncture or the like (described in Lazorthes et al. Advances in Drug Delivery Systems and Applications in Neurosurgery, 143–192 and Omaya et al., Cancer Drug Delivery, 1: 169–179, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of a therapeutic agent to any of the above mentioned sites can be achieved by direct injection of the encapsulated therapeutic agent. For injection, the encapsulated therapeutic agents of the invention can be formulated in liquid solutions, preferably in physiologically compatible buffers such as Hank's solution or Ringer's solution. In addition, the agents may be formulated in solid form and redissolved or suspended immediately prior to use. Lyophilized forms are also included. The injection can be, for example, in the form of a bolus injection or continuous infusion of the encapsulated therapeutic agent.

In one embodiment of the invention, said encapsulated therapeutic agent is administered by lateral cerebro ventricular injection into the brain of a subject in the inclusive period from the time of the stroke or TBI to 100 hours thereafter. The injection can be made, for example, through a burr hole made in the subject's skull. In another embodiment, said encapsulated therapeutic agent is administered through a surgically inserted shunt into the cerebral ventricle of a subject in the inclusive period from the time of the ischemic event to 100 hours thereafter. Preferably, the injection is made into the lateral ventricles, which are larger, even though injection into the third and fourth smaller ventricles can also be made.

In yet another embodiment, said encapsulated therapeutic agent is administered by injection into the cisterna magna, or lumbar area of a subject in the inclusive period from the time of the ischemic event to 100 hours thereafter.

Duration of administration

The method of the invention permits an initial burst of delivery followed by non "zero order" sustained delivery of the therapeutic agent to a subject in vivo, after administering the encapsulated therapeutic agent to the subject, wherein the duration of the sustained delivery can be varied depending upon the concentration of therapeutic agent and pharmaceutically acceptable polymer used to form the complex.

As used herein, the term "initial burst" is intended to include a sudden intense release of a therapeutic agent in vivo.

As used herein, the term "sustained delivery" is intended to include continual delivery of a therapeutic agent in vivo over a period of time following administration, preferably at least several days, a week or several weeks. Sustained delivery of the therapeutic agent can be demonstrated by, for example, the continued therapeutic effect of the agent over time (e.g., for an anti-inflammatory agent, sustained delivery of the agent can be demonstrated by continued reduction of fluid accumulation in the brain over time). Alternatively, sustained delivery of the agent may be demonstrated by detecting the presence of the agent in vivo over time.

Preferably, the encapsulated therapeutic agent provides sustained delivery of the therapeutic agent to a subject for less than 30 days after the encapsulated therapeutic agent is administered to the subject. More preferably, the encapsulated therapeutic agent provides sustained delivery of the therapeutic agent to a subject for one, two or three weeks after the therapeutic agent is administered to the subject.

As used herein the language "non zero order sustained delivery" is intended to include sustained delivery that does not occur at a constant (linear) rate.

The pharmaceutical formulation, used in the method of the invention, contains a therapeutically effective amount of the therapeutic agent. A "therapeutically effective amount" refers to an amount effective, at dosages and for periods of time necessary, to achieve the desired result. A therapeutically effective amount of the therapeutic agent may vary according to factors such as the disease state, age, and weight of the subject, and the ability of the therapeutic agent (alone or in combination with one or more other agents) to elicit a desired response in the subject. Dosage regimens may be adjusted to provide the optimum therapeutic response. A therapeutically effective amount is also one in which any toxic or detrimental effects of the therapeutic agent are outweighed by the therapeutically beneficial effects. A non-limiting range for a therapeutically effective amount of the therapeutic agent is 0.1–1.0 mg/kg. It is to be noted that dosage values may vary with the severity of the condition to be alleviated. It is to be further understood that for any particular subject, specific dosage regimens should be adjusted over time according to the individual need and the professional judgment of the person administering or supervising the administration of the encapsulated therapeutic agent, and that dosage ranges set forth herein are exemplary only and are not intended to limit the scope or practice of the claimed composition.

The following examples which further illustrate the invention, should not be construed as limiting. The contents of all references, pending patent applications and published patents, cited throughout this application (including the "Background" Section) are hereby expressly incorporated by reference.

EXAMPLE

The Delivery of Therapeutic Agent(s) to the Brain Using a Polymeric Delivery System The rat MCA-O (middle cerebral artery occlusion) model was prepared essentially as described in Bartus et al. (*J. of Cerebral Blood Flow and Metabolism* 14:537–544, 1994). Briefly, male Sprague-Dawley rats, were anesthetized with a 4 ml/kg mixture of ketamine (25 mg/ml), xylazine (1.3 mg/ml), and acepromazine (0.33 mg/ml) after premedication with atropine methylbromide (0.1 mg/kg, i.p.). The common carotid arteries (CCA) were dissected free of the vagus nerve and surrounding fascia through a ventral midline cervical incision. To locate the left MCA, a 1.0-cm vertical incision was made in the left temporal region midway between the lateral canthus of the eye and the external auditory canal. The temporalis muscle was bisected and the superior attachments were retracted in both rostral and caudal directions. The bifurcation (of frontal and parietal branches) of the MCA was visualized through a craniotomy made 3–4 mm in front of the junction of the zygomatic arch and the squamosal bone. The parietal branch was occluded up to 2.0 mm distal from the bifurcation using a single 10-0 suture (Ethicon Inc., Somerville, N.J., U.S.A.), taking care to include in the occlusion any major branches that may bifurcate from the parietal branch within 2.0 mm of the frontal/parietal bifurcation. Immediately following permanent ligation of the parietal branch of the left MCA, the CCAs were temporarily occluded bilaterally, using atraumatic aneurysm clips (Roboz Surgical Instruments, Rockville, Md., U.S.A.). The temporalis muscle was then sutured with a single 3-0 nylon stitch and the skin closed with three surgical wound clips. One hour later, the aneurysm clips were removed from the CCAs (allowing spontaneous reperfusion) and the wound was closed.

Body temperature was regularly monitored (via rectal probe), recorded, and maintained (normothermic) throughout and following the MCA-O procedure by placing the animals on heating pads. If an animal's temperature fell below 36° C. or rose above 38° C. and could not be quickly corrected, the animal was eliminated from the study. Animals were returned to their home cages once their righting reflex was established.

The rat MCA-O model was used to examine the efficacy of drugs, delivered to the brain ventricles either via a pump or by injection after encapsulation in a polymeric delivery vehicle (a gelatin sponge, sold as Gelfoam by The Upjohn Company, Kalamazoo, Mich.). In FIG. 1, the results from the experiments testing the delivery of superoxide dismutase are depicted. Each experiment encompassed three groups of animals. In group #1, saline was delivered into the brain ventricles of the rat as a control. In group #2, a low dose (6,800 units/ml) of SOD was delivered, and in group #3, a high dose (13,600 units/ml) of SOD was delivered. The results indicate that at a high dose, the gel foam delivery of SOD is as efficient as the pump delivery in inhibiting infarction.

Figure 2:
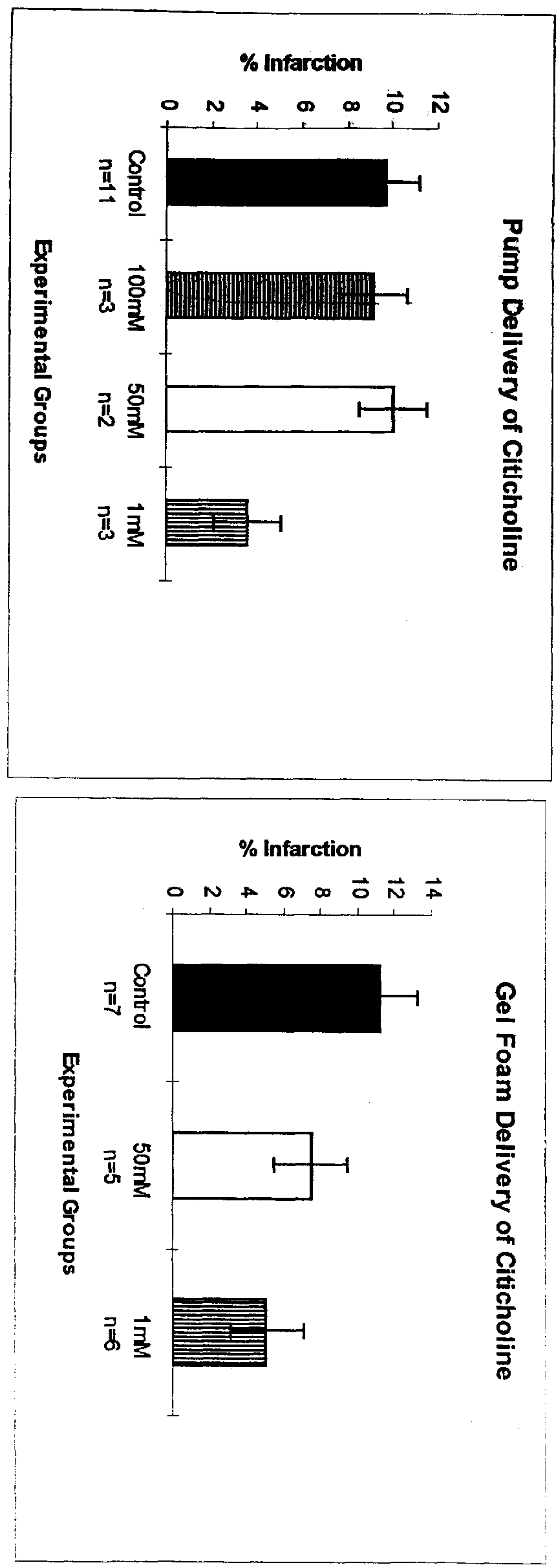
FIG. 2, is a graph depicting local delivery of citicholine in the cerebrospinal fluid (CSF) of the MCA-O rat either via a pump (left graph) or by injection after encapsulation in a polymeric delivery vehicle (gel foam) (right graph). Four groups of animals were used: A saline control (black bar), a group having a final cerebrospinal fluid (CSF) citicholine concentration of 100 mM (horizontal striped bar), a group having a final cerebrospinal fluid (CSF) citicholine concentration of 50 mM (white bar), and a group having a final cerebrospinal fluid (CSF) citicholine concentration of 1 mM (vertical striped bar).

In FIG. 2, the results from the experiments testing the delivery of citicholine are depicted. Each experiment encompassed four groups of animals. In group #1, saline was delivered into the brain ventricles of the rat as a control. In group #2, citicholine was delivered at a final concentration of 100 mM, in group #3, citicholine was delivered at a final concentration of 50 mM, and in group #4, citicholine was delivered at a final concentration of 1 mM. The results indicate that the gel foam delivery of citicholine is more efficient at inhibiting infarction as compared to the pump delivery.

EQUIVALENT

Those skilled in the art will recognize, or be able to ascertain using no more than routine experimentation, many equivalents to the specific embodiments of the invention described herein. Such equivalents are intended to be encompassed by the following claims.

We claim:

1. A method for universally distributing a therapeutic agent to the brain for treatment, comprising administering to a subject a therapeutic agent such that universal distribution of the agent to the brain occurs, wherein the therapeutic agent is intrathecally introduced into the cerebrospinal fluid of the subject, in an encapsulated form at an entry region which is not the lumbar region.

2. A method for treating stroke, comprising administering to a subject a therapeutic agent such that universal distribution of the agent to the brain occurs, wherein the therapeutic agent is administered by introduction into the cerebrospinal fluid of the subject, in an encapsulated form.

3. A method for treating Traumatic Brain Injury (TBI), comprising administering to a subject a therapeutic agent such that universal distribution of the agent to the brain occurs, wherein the therapeutic agent is administered by introduction into the cerebrospinal fluid of the subject, in an encapsulated form.

4. The method of claim 1, wherein the subject is a mammal.

5. The method of claim 4, wherein the mammal is a human.

6. The method of claim 1, wherein the therapeutic agent is encapsulated in a polymer.

7. The method of claim 6, wherein the polymer is selected from the group consisting of naturally derived polymers, such as albumin, alginate, cellulose derivatives, collagen, fibrin, gelatin, and polysaccharides.

8. The method of claim 6, wherein the polymer is selected from the group consisting of synthetic polymers such as polyesters (PLA, PLGA), polyethylene glycol, poloxomers, polyanhydrides, and pluronics.

9. The method of claim 1, wherein the therapeutic agent is selected from the group consisting of free radical scavengers and antioxidants, nonsteroidal anti-inflammatory drugs (NSAIDS), steroidal anti-inflammatory agents, calcium channel blockers, NMDA antagonists, and citicholine.

10. The method of claim 2, wherein the therapeutic agent, is introduced intrathecally.

11. The method of claim 10, wherein the therapeutic agent, in an encapsulated form, is introduced into a cerebral ventricle.

12. The method of claim 10, wherein the therapeutic agent, in an encapsulated form, is introduced into the cisterna magna.

13. The method of claim 10, wherein the therapeutic agent, in an encapsulated form, is introduced into the lumbar region.

14. The method of claim 2, wherein the therapeutic agent, in an encapsulated form, is administered to a subject from the time of the traumatic incident to 100 hours after the incident, wherein the traumatic incident comprises TBI or stroke.

15. The method of claim 2, wherein the therapeutic agent, in an encapsulated form, is administered to a subject from the time of the traumatic incident to 24 hours after the incident, wherein the traumatic incident comprises TBI or stroke.

16. The method of claim 2, wherein the therapeutic agent, in an encapsulated form, is administered to a subject from the time of the traumatic incident to 12 hours after the incident, wherein the traumatic incident comprises TBI or stroke.

17. The method of claim 2, wherein the therapeutic agent, in an encapsulated form, is administered to a subject from the time of the traumatic incident to 6 hours after the incident, wherein the traumatic incident comprises TBI or stroke.

18. The method of claim 1, wherein the therapeutic agent, in an encapsulated form, provides an initial burst followed by sustained delivery of the therapeutic agent to a subject for at least one week after the therapeutic agent, in an encapsulated form, is administered to the subject.

19. The method of claim 1, wherein the therapeutic agent, in an encapsulated form, provides an initial burst followed by sustained delivery of the therapeutic agent to a subject for at least two weeks after the therapeutic agent, in an encapsulated form, is administered to the subject.

20. The method of claim 1, wherein the therapeutic agent, in an encapsulated form, provides an initial burst followed by sustained delivery of the therapeutic agent to a subject for at least three weeks after the therapeutic agent, in an encapsulated form, is administered to the subject.

21. A pharmaceutical composition intended for administration into the cerebrospinal fluid of a subject, comprising a therapeutic agent encapsulated in a pharmaceutically acceptable polymer, wherein the therapeutic agent is present at therapeutically effective concentrations which, if injected into the cerebrospinal fluid of a subject suffering from stroke will contribute to the amelioration of the disorder.

22. A pharmaceutical composition intended for administration into the cerebrospinal fluid of a subject, comprising a therapeutic agent encapsulated in a pharmaceutically acceptable polymer, wherein the therapeutic agent is present at therapeutically effective concentrations which, if injected into the cerebrospinal fluid of a subject suffering from TBI will contribute to the amelioration of the disorder.

* * * * *